(12) United States Patent
Alt et al.

(10) Patent No.: US 6,370,427 B1
(45) Date of Patent: Apr. 9, 2002

(54) METHOD AND APPARATUS FOR DUAL CHAMBER BI-VENTRICULAR PACING AND DEFIBRILLATION

(75) Inventors: Eckhard Alt, Ottobrunn (DE); Lawrence J. Stotts, Lake Jackson; Richard Sanders, Houston, both of TX (US)

(73) Assignee: Intermedics, Inc., St. Paul, MN (US)

( * ) Notice: Subject to any disclaimer, the term of this patent is extended or adjusted under 35 U.S.C. 154(b) by 0 days.

(21) Appl. No.: 09/121,523

(22) Filed: Jul. 23, 1998

(51) Int. Cl.[7] ................................................. A61N 1/39
(52) U.S. Cl. ................... 607/4; 607/5; 607/9; 607/121; 607/120
(58) Field of Search ........................... 607/4, 5, 9, 122, 607/120, 121

(56) References Cited

U.S. PATENT DOCUMENTS

| | | | | |
|---|---|---|---|---|
| 4,033,357 A | * | 7/1977 | Helland et al. | 607/122 |
| 4,928,688 A | * | 5/1990 | Mower | 607/9 |
| 5,050,601 A | | 9/1991 | Kupersmith et al. | |
| 5,224,475 A | | 7/1993 | Berg et al. | |
| 5,514,161 A | * | 5/1996 | Limousin | 607/9 |
| 5,540,727 A | | 7/1996 | Tockman et al. | |
| 5,720,768 A | * | 2/1998 | Verboven-Nelissen | 607/9 |
| 5,902,324 A | | 5/1999 | Thompson | 607/9 |
| 6,067,470 A | | 5/2000 | Mower | 607/5 |

* cited by examiner

*Primary Examiner*—George R. Evanisko
(74) *Attorney, Agent, or Firm*—Blank, Rome, Comisky & McCauley, LLP (57) ABSTRACT

Device and method are disclosed in which leads with pacing and defibrillating electrodes are implanted into both the right and left ventricles of a patient's heart to enable simultaneous pacing of both ventricles to reduce the width of the QRS complex of the patient's cardiac activity to a more normal duration, and, when appropriate, to apply electrical shock waveforms to both ventricles simultaneously for lower energy defibrillation of the ventricles. In applying the defibrillation therapy, the defibrillating electrode in the left ventricle may be used as the anode and the defibrillating electrode in the right ventricle may be used as the cathode, or both ventricular defibrillating electrodes may be the anode and the metal case in which the shock waveform generator is implanted may be the cathode. Implanting a lead with pacing and defibrillating electrodes in the right atrium enables selective pacing and defibrillation of the atria, in which atrial fibrillation is treated by applying the shock waveform across the right atrial and left ventricular defibrillation electrodes.

33 Claims, 2 Drawing Sheets

METHOD AND APPARATUS FOR DUAL CHAMBER BI-VENTRICULAR PACING AND DEFIBRILLATION

BACKGROUND OF THE INVENTION

The present invention relates generally to implantable medical devices for treating cardiac dysrhythmias, and more particularly to a multi-mode device which is adapted to provide bi-ventricular therapy to the patient's heart in response to sensing applicable dysrhythmias.

Progress in medicine is based largely on progress in the technology of devices and apparatus for administering therapy. For example, significant advances in design techniques that have resulted in continuing reductions in the size of implantable defibrillators, including size of the function generator itself as well as in the heart leads associated therewith, have led to a capability to implant defibrillators at considerably lower risk to patients. During the first few years following the advent of implantable defibrillators, implant procedures required general anesthesia and thoracotomy, and the patient was faced with all of the risks associated with opening the chest cavity. The mortality rate of the procedure tended to limit widespread use of the device.

In recent years, with lower defibrillation thresholds (DFTs) and reduction in high voltage capacitor and battery sizes, smaller and more easily implantable devices have been developed, which have allowed this operation to be performed today under only local anesthesia. Smaller diameter and more easily inserted transvenous lead systems have overcome the need for a thoracotomy, and mortality associated with the procedure has been concomitantly reduced to less than one percent. The cosmetic aspects of such an implantation have also improved, with device size and weight allowing it to be implanted in the pectoral region that had previously been reserved for devices capable of only pacing functions, rather than the lower abdomen.

Nevertheless, at least two issues remain to be resolved with respect to present-day implantable defibrillators. For one thing, despite size reduction owing to the aforementioned advances in technology, the devices are still relatively large. At present, the limitations on size reduction are primarily attributable to the magnitude of energy required to achieve successful defibrillation with an adequate safety margin. A capacity for energy delivery of 25 to 32 joules (J), on average, currently remains the standard for implantable defibrillators. This minimum energy requirement mandates production and use of devices ranging from 40 to 50 cubic centimeters (cc) in volume and 80 to 100 grams (g) in weight.

Another issue that remains to be resolved is the provision of a continuously uniform, homogeneous electric field distribution during application of the relatively high energy defibrillating shocks to the heart. Studies performed on animals and humans indicate that to achieve a successful defibrillation with a lowered energy content shock requires a substantially uniform electric field distribution throughout the portion of the mass of cardiac tissue involved in the fibrillation. Lower energy requirement and fewer shocks to achieve a successful defibrillation are important not only from the standpoints of further size reduction and maintenance of an adequate reserve to increase the interval between defibrillator replacements, but also to avoid potential damage to the heart and skeletal frame of the patient that can occur with frequent or repeated application of high energy shocks.

Under typical defibrillator implant conditions, a coil is introduced into the right ventricle to serve as one electrode or pole, and the defibrillator case (or "can," as it is often called in the art) that houses the batteries, capacitors, electronic components and circuitry is used as the second pole for the current path during the defibrillation shock. As noted above, the defibrillator case can now be implanted in the pectoral region, usually on the left side, to provide a more effective defibrillation pathway. This is desirable from the standpoint of the implant technique and the cosmetic aspect, but produces an energy and electric field distribution that is not equal, uniform or homogeneous throughout the region of the heart involved in the fibrillation. Measurements performed by the applicants have demonstrated that during application of a shock waveform using standard case, lead and defibrillation coil placements, a field of significantly lower energy (in volts (v) per centimeter (cm), i.e., v/cm) is present at the apex of the left ventricle compared to certain other regions of the heart such as the right ventricular outflow tract. The average electric field strength in the latter region is five to eight times greater than at the apex of the left ventricle.

In practice, then, because a relatively lower energy field is present at some regions that may be critical to defibrillation, the energy gradient sufficient to achieve successful defibrillation by application of the shock waveform mandates an adequate energy level in those regions and, by extension, a considerably higher electric field density in the normally higher energy field locations as well. The result is a further skewing of the inequality or inhomogeneity of the electric field distribution in the strategically important regions.

In one of its aspects, the present invention provides improvements in lead and electrode placements to assist in developing an equal, homogeneous field distribution during application of a defibrillation shock to the heart.

Another problem encountered with present day defibrillators, however, is that despite their capability to provide adequate therapy for sudden electrical instabilities of the cardiac function, they are not similarly capable of providing therapy for an underlying hemodynamically-compromised ventricular function. This means that the patient may suffer an ongoing deficiency in cardiac output, for example, even though the device is effective in correcting isolated events of fibrillation or pacing dysrhythmias.

Clinical investigation performed on patients who suffer from heart failure (i.e., inability of the heart to pump the required amount of blood) indicates that for a certain subset of these patients simultaneous stimulation of the left and right ventricles may be advantageous. In the cardiac cycle, a P wave of the subject's electrocardiogram (ECG) is produced by a depolarization of the atrial fibers just before they contract, and, when the cardiac impulse reaches the ventricular fibers to stimulate them into depolarization, a QRS complex is produced just before contraction of the ventricular walls. This is followed by a T wave which is indicative of the electrical activity occurring upon repolarization of the ventricular fibers. Simultaneous stimulation of the left and right ventricle would be beneficial therapy to patients whose ECG displays a marked desynchronization in contraction of the two ventricular chambers. In such cases, it is observed that after a right ventricular stimulation, considerable time may elapse for the cardiac impulse to travel from the apex of the right ventricle through the septum and to the free wall of the left ventricle, with the septum contracting earlier than the latter.

Consequently, the mechanical forces of the ventricular contraction are less favorable for an effective hemodynamic output in such patients. The duration or width of the QRS complex may increase because of an injury to the Purkinje fibers that inhabit and stimulate the ventricular septum and the lateral ventricular walls, and which could therefore increase the time for the impulse to spread throughout the ventricular walls. Patients who display a lack of ventricular synchronization primarily exhibit a wide QRS complex indicative of a bundle branch block—generally a left bundle branch block. Rather than the normal QRS complex width that ranges between 80 to 120 milliseconds (ms), the width of the QRS complex for these patients ranges between 140 and 200 ms.

It is a principal aim of the present invention to provide a method and apparatus for improved hemodynamic performance in patients with heart failure, utilizing an implantable defibrillator of reduced size and increased efficacy which produces a substantially uniform, homogeneous electric field upon application of a defibrillation shock to the heart.

SUMMARY OF THE INVENTION

The present invention provides simultaneous pacing of the left and right ventricles of the patient's heart, and, unlike the prior art in which a pacing lead is inserted into the right ventricle only (through the right atrium and tricuspid valve), a separate pacing lead is also inserted into the left ventricle. Defibrillation coils provided on separate lead wires may be sheathed in respective ones of the two pacing leads for insertion therewith. A defibrillation coil is introduced on a lead into the right ventricle and is seated so that a sensing and stimulating electrode at its distal end resides at the apex of that chamber. An atrial defibrillation coil is inserted on another lead into the right atrium to enable stimulation of the atrial chamber, as appropriate, with pacing pulses and for application of defibrillating shocks. These right chamber (ventricular and atrial) leads enable cardiac pacing stimulation in VVI, VVI-R, DDD, DDD-R, AAI, AAI-R, and other modes, and permit application of defibrillation shocks between the respective coil and the active can or case of the device.

According to the invention, a second ventricular lead is placed in the left ventricle by needle puncture of the arteria subclavia (left subclavian artery) or the brachiocephalic artery, and advancement into the left ventricular chamber through the aortic valve. To avoid interference with the mechanical function of the aortic valve during retrograde passage of this lead into the left ventricle, or thereafter while in place, the lead should be of relatively smaller diameter than traditional ventricular leads (e.g., in a range of 6 to 7 French, or less). Also, its outer surface should be composed of electrically insulative material of very low thrombogenicity (e.g., high performance silicone or polyurethane). Local formation of a thrombus that could embolize and travel to the brain through the aortic valve is additionally avoided by use of platelet (thrombocyte) inhibitors (e.g., preferably ticlopidine, but alternatively or additionally aspirin, GPIIb/IIIa blockers or other inhibitors of the fibrinogen receptor), and by plasmatic coagulation inhibitors (e.g., heparin and hirudin). Such inhibitors are preferably administered for a duration of about one to three months following the surgical procedure. This time period should be adequate to allow a build-up of protective connective tissue around the electrode and also to prevent adhesion of the lead body in the vicinity of the aortic valve.

The left ventricular lead is otherwise of similar construction to the right ventricular lead, and enables pacing stimulation of the left ventricle simultaneously with pacing stimulation of the right ventricle, with resulting improvement in hemodynamics, in large measure by virtue of more organized contraction and avoidance of mitral regurgitation. It is also possible, albeit difficult, to place a lead with a pacing electrode in the left atrium. This is achievable, preferably, by inserting the lead into the left atrium by access from the adjacent distal coronary sinus, or, alternatively, by access through the atrial septum wall from the right atrium. This enables simultaneous pacing of the right and left atria, and synchronization of the simultaneous pacing of the right and left ventricles according to the preset A-V delay, in a DDD mode, plus the capability for bi-ventricular defibrillation.

Most importantly, placement of a defibrillation coil on a lead in the left ventricle allows a considerable reduction of the energy requirement necessary to achieve a successful shock (i.e., termination of ventricular fibrillation, and return to sinus rhythm), with a threshold (DFT) that may be as low as only 2 to 3 joules (J.). To that end, the defibrillation shocks may be applied solely between the two (i.e., right and left) ventricular coil electrodes, and by creating a substantially equal and homogeneous electric field distribution around them through the two ventricular chambers. Alternatively, if individual parameters of thorax geometry and the heart make it necessary or desirable, the shock waveform may be applied between both ventricular coils, operating as one pole, and the device case acting as the other pole. In this alternative configuration, defibrillation is achieved with a somewhat higher DFT than the other, but still considerably below the thresholds seen in the prior art.

Thus, the present invention permits defibrillators with maximum available energy output capability of only 15 joules or less to be implanted with reasonable assurance of successful defibrillation with quite adequate safety margin, even in relatively enlarged hearts. Such low energy requirement means that devices weighing considerably less than 50 grams (g.) and having volumes of less than even 30 cubic centimeters (cc.) can be implemented for this purpose, so that the function generator portion of the device can be sized on the same order as devices that functioned solely as the DDD pacemaker of recent vintage. Hemodynamic improvement attained by simultaneously pacing the left and right ventricles also reduces the occurrence of fibrillation, and thus, the need for defibrillation.

In one aspect of the invention, an implantable medical interventional device is adapted to provide therapy to a patient in whom the device is implanted to treat cardiac dysrhythmias. The device includes function generating means for providing a plurality of functions corresponding to different levels of therapy for treatment of sensed dysrhythmias, including a pulse generator adapted for pacing the patient's heart by generating stimulating electrical pulses therefor. A pair of thin leads is coupled to the pulse generator and sized for insertion respectively into the left and right ventricles of the patient's heart when the device is implanted, for application of the stimulating electrical pulses thereto. Each of the leads includes an electrode located on the respective lead for positioning in stimulating relation to cardiac tissue in a respective one of the ventricles and, when energized together by the pulse generator, to simultaneously pace the left and right ventricles.

The lead adapted for insertion into the left ventricle includes an insulative sheath composed of a material of low thrombogenicity, such as a material selected from a group which includes high performance silicone and polyurethane. Also, the insulative sheath is coated at least in part with a biodegradable material to inhibit thrombus formation on the respective lead. The biodegradable material coating may be impregnated with at least one platelet inhibitor (preferably, iloprost) for timed release during disintegration of the coating. The coating may additionally or alternatively be impregnated with a plasmatic coagulation inhibitor such as heparin or hirudin for timed release.

The function generator includes a shock generator adapted for defibrillating the patient's heart by generating higher voltage electrical shock waveforms. Each of the leads includes a defibrillation coil coupled to the shock generator and located on its lead to be positioned within a respective ventricle to apply an electrical shock waveform to establish a substantially homogeneous electric field of sufficient electrical energy through the ventricles for defibrillation thereof. The defibrillation coils constitute defibrillation poles, and when energized simultaneously the defibrillation coil in the left ventricle is the anode and the defibrillation coil in the right ventricle is the cathode. Alternatively, the ventricular defibrillation coils constitute a single defibrillation pole and are energized simultaneously as an anode, and the metal case within which the function generator is housed constitutes a second defibrillation pole which is energized together with the defibrillation coils as a cathode. An atrial pacing lead includes a pacing electrode coupled to the pulse generator, and a defibrillation coil adapted to be positioned within the right atrium and coupled to the shock generator for defibrillation of the atria.

A variation of the invention is implemented in an implantable pacemaker that includes a pulse generator, a right ventricular pacing lead with an electrode coupled to the pulse generator for positioning in the right ventricle to deliver stimulating pacing pulses from the generator thereto, a left ventricular pacing lead with an electrode coupled to the pulse generator for positioning in the left ventricle to deliver stimulating pacing pulses from the generator thereto, and means for applying selected ones of the stimulating pacing pulses to the right and left ventricular pacing leads for stimulating the ventricles simultaneously. The pacemaker also includes an atrial pacing lead with an electrode coupled to the pulse generator and positioned in the right atrium to deliver stimulating pacing pulses thereto, and means for applying selected ones of the stimulating pacing pulses to the atrial pacing lead, timed for stimulating the atria.

A variation of the invention is implemented in an implantable defibrillator, which includes a shock generator for generating electrical shock waveforms, a right ventricular lead with a defibrillation electrode coupled to the shock generator for positioning in the right ventricle to deliver electrical shock waveforms thereto, a left ventricular lead with a defibrillation electrode coupled to the shock generator for positioning in the left ventricle to deliver electrical shock waveforms thereto, and means for selectively applying electrical shock waveforms of predetermined energy content simultaneously to the right and left ventricular defibrillation electrodes to establish a substantially homogeneous electric field distribution in the ventricles for defibrillation thereof. A right atrial lead of the defibrillator includes a defibrillation electrode coupled to the shock generator for positioning in the right atrium to deliver electrical shock waveforms thereto, and the selectively applying means applies the electrical shock waveforms between the right atrial defibrillation electrode and one of the right ventricular defibrillation electrode, the left ventricular defibrillation electrode, and the metal case of the shock generator, for defibrillation of the atria.

Also according to the invention, a device-implemented method of treating cardiac dysrhythmias is performed with an implantable medical interventional device adapted to deliver therapy to an implant patient. The device possesses the capability to provide pacing therapy to the patient's heart, and the method includes the steps of sensing a need for ventricular pacing, and responding to the sensed need by delivering pacing pulses simultaneously to both ventricles of the patient's heart. The device-implemented method also includes the steps of sensing ventricular fibrillation, and responding to the sensed ventricular fibrillation by delivering an electrical shock waveform simultaneously to both ventricles to establish an electric field of relatively uniform distribution and sufficient electrical energy through the ventricles for defibrillation thereof.

Another aspect of the invention resides in a method for providing therapy to a patient from a medical interventional device to treat cardiac dysrhythmias, wherein the device performs a plurality of functions corresponding to different levels of therapy for treatment of sensed dysrhythmias. The device responds to each different type of sensed dysrhythmia to generate an electrical waveform therapy among a variety of therapies appropriate to terminate the respective sensed dysrhythmia, including at least electrical pulse and shock waveform therapies therefor. The method includes implanting an electrical lead with an electrode to deliver at least one of the pulse and shock waveform therapies in each of the right and left ventricles, and electrically connecting each lead to the device to enable its electrode to receive at least one of the therapies.

In the method, prior to implanting the lead, at least a portion of the lead to be implanted in the left ventricle is coated with a biodegradable carrier impregnated with a thrombus inhibitor adapted to be time-released into blood in the locality of the portion of the lead in the left ventricle during disintegration of the carrier, to avoid embolization of a thrombus thereat. The method includes selecting the biodegradable carrier to degrade harmlessly in the blood with negligible systemic impact, and selecting at least one of ticlopidine and aspirin as concomitant oral therapy and intravenous or subcutaneous administration of heparin and hirudin, as the thrombus inhibitor. Also, at least one physical parameter of the biodegradable carrier is selected to fix complete disintegration of the carrier within a period of from about one month to about three months from the time of implanting the lead, for time-release of the thrombus inhibitor over the period. The electrical lead is placed in the left ventricle by puncturing one of the subclavian and brachiocephalic arteries, inserting the lead through the puncture, and advancing the lead through the aortic valve into the left ventricle until the electrode is properly located therein. Each ventricular lead includes both a pacing electrode at the distal end of the lead and a defibrillating electrode proximal of the pacing electrode, and advancement of each lead into the respective ventricle includes placing the pacing electrode in proximity to excitable cardiac tissue of the ventricle.

In the method, the right and left ventricles are paced simultaneously, whereby to reduce the duration of the QRS complex of the patient's electrocardiogram. Shocks are applied to the defibrillating electrodes of both the right and left ventricular leads simultaneously, whereby to improve uniformity of the electric field distribution through the ventricles to terminate ventricular fibrillation. And shocks are applied to the defibrillating electrodes of both the right atrial lead and the left ventricular lead simultaneously to terminate atrial fibrillation. Also, the local ECG is detected at the left and right ventricles, and the size, morphology and other characteristics thereof are compared to discriminate the origin of the tachycardia, such as to distinguish ventricular and supraventricular tachycardias from one another.

BRIEF DESCRIPTION OF THE DRAWINGS

The above and still further aims, objects, aspects, features and attendant advantages of the present invention will become apparent from a consideration of the following detailed description of the presently contemplated best mode of practicing the invention, by reference to a preferred embodiment and method, taken in conjunction with the accompanying drawings, in which.

DETAILED DESCRIPTION OF THE PREFERRED EMBODIMENT AND METHOD OF THE INVENTION

Figures 1, 2:
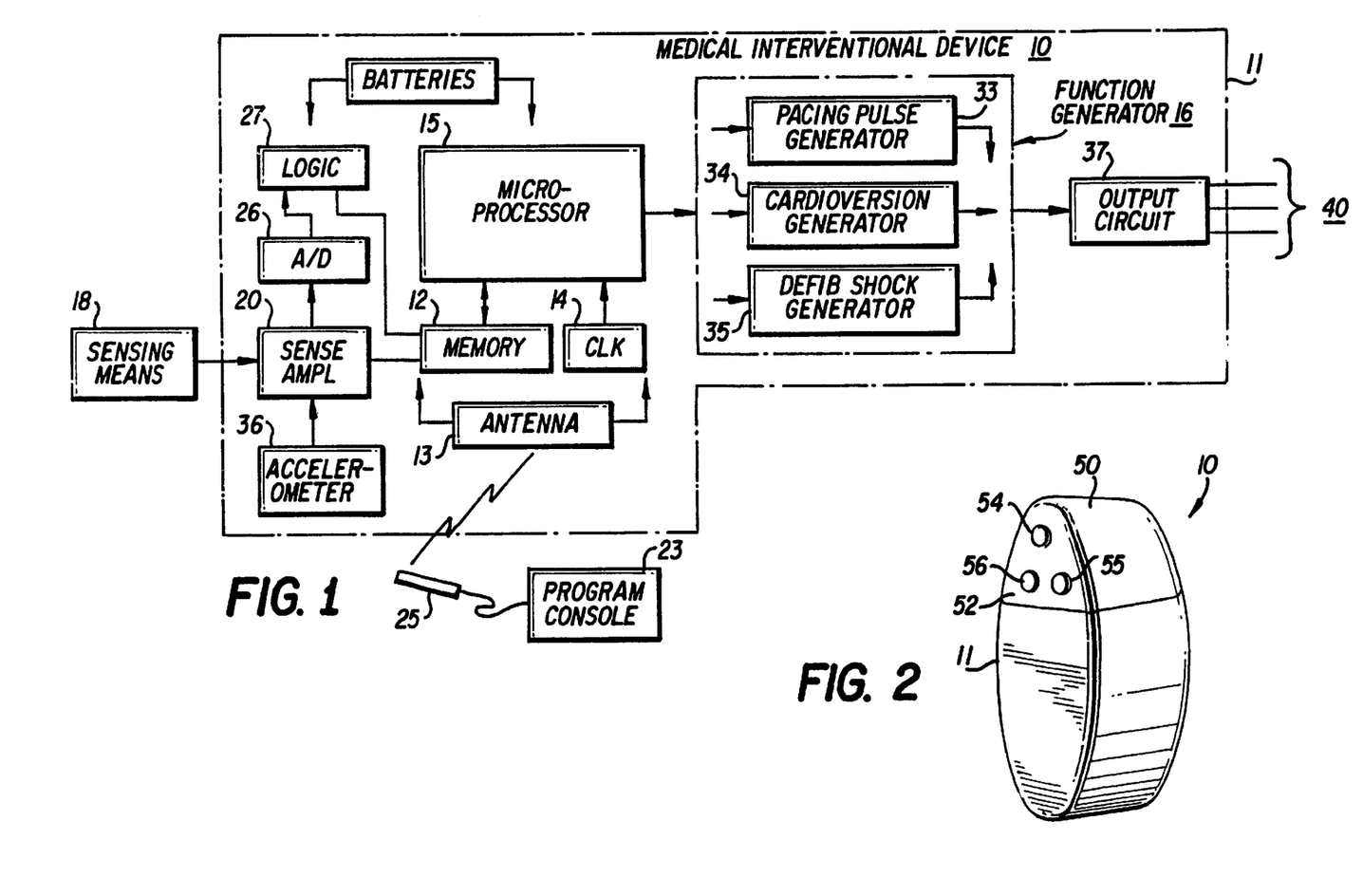
FIG. 1 is a block diagram of an embodiment of an implantable medical interventional device in which the present invention is used.
FIG. 2 is a perspective view of an exemplary header of the implantable medical interventional device of FIG. 1.

FIG. 1 is a block diagram of an exemplary embodiment of an implantable medical interventional device 10 having capabilities of pacing, cardioversion and defibrillation, all of the components of which may be entirely conventional except as otherwise described herein, in which the present invention may be used. Device 10 includes a function generator 16 for providing a plurality of functions corresponding to different levels of therapy for treatment of dysrhythmias. These may include generating relatively low energy pulse waveforms for pacing therapy including anti-bradycardia and anti-tachycardia pacing, moderate energy shock waveforms for cardioversion therapy, and relatively higher energy shock waveforms for defibrillation therapy. An output circuit of function generator 16 supplies the designated therapy to a set of leads and electrodes for delivering it to designated chambers of the heart. The output circuit may include capacitors and high voltage switches for producing high energy defibrillating shocks, and the electrodes may include the biocompatible metal housing (i.e., the case, or "can") 11 of device 10 as an active electrode, if desired for a particular type of therapy.

Function generator 16 performs its therapy-generating and delivery functions under the control of a microprocessor 15 containing arithmetic, logic, and control circuitry in conjunction with peripheral circuits or subsystems such as memory 12, clock 14, etc., as a central processing unit (CPU) for the device. The microprocessor responds to instructions to perform high speed, real-time functions for controlling the operation of the function generator. The memory units may be written to and read from, by telemetry between device 10 and a program console 23 through a wand 25 via antenna 13, and with related software, so that the microprocessor performs desired functions. These functions may then be varied by means of the programming console, or programmer 23, by the device manufacturer or the patient's attending physician.

Sensing means 18 within or outside the device housing 11 detects any of various physiologic parameters indicative of the patient's cardiac functions and physical status, to sense dysrhythmias and initiate appropriate response mechanisms from the device. Sensed parameters may include the patient's electrogram (ECG), heart rate and/or rhythm, status of rest, exercise or activity of the patient (e.g., using an accelerometer 36 within the case 11, as here, or in its own separate housing), etc., the latter enabling the device 10 to provide a rate adaptive response, as well as other dysrhythmia correction therapies. The sensing means also includes conventional sensors of physiological signals for detecting congestive heart failure, for example.

Sense amplifier circuitry 20 responds to analog input signals 22 from the sensors (sensing means) 18 for processing thereof. The processed signals are converted to digital format by an analog-to-digital (ASD) converter 26 and the digital output is applied to logic circuitry 27 which interacts with microprocessor 15 and memory 12 to execute programmed operating instructions. If the sensed signals are indicative of a dysrhythmia, the device generates the appropriate conventional pacing, cardioverting, or defibrillating electrical waveforms from blocks 33, 34 or 35, respectively, of function generator 16 under the control of the microprocessor in response to the specific type of dysrhythmia. When no immediate demand for therapy is being imposed, the microprocessor reverts to a "sleep" mode, to be awakened at any time a therapy requirement is indicated by the sense signals.

Pacing therapy modes may include combinations of single and dual chamber sensing, pacing, and electrical response functions for treating bradycardia and pathologic tachycardia, as well for providing rate-adaptive pacing using the accelerometer 36 as an activity/exercise sensor. Additionally, the device is preferably programmed with memory modes and diagnostics including acquisition of real-time ECG morphology from intracardiac and surface leads, and trends thereof over time, as well as activation of memory or Holter functions in conjunction with various events. For example, the device may be programmed to undergo mode switching from DDD to VVI-R pacing when the patient is experiencing episodes of atrial fibrillation. In that event, the device will switch from DDD to VVI pacing mode automatically when a pathologic atrial tachycardia is detected, and reverts from VVI to DDD operation automatically when physiologic atrial tachycardia is sensed, distinct from the pacing therapy modes selected by programming the device. The atrial ECG morphology, for example, is stored in the form of atrial signals detected prior to, during and after a cardiac dysrhythmia event, and this morphology is retrieved from the implanted device memory at a later time using telemetry and the external program console. This enables interpretation of cardiac activity that led up to the event of interest, the onset of the event, and the response of the patient's heart to the electrical waveform therapy subsequently delivered by the implanted device.

Some therapeutic output waveforms produced by the microprocessor-based function generator 16 may be used to treat more than one rhythm disorder. For example, a burst of pulses may be used for therapy to terminate a tachycardia, or may be one among a hierarchy of therapy responses selectively delivered to perform cardioversion. The waveform representing the appropriate therapy to treat the sensed dysrhythmia within the designed capabilities of device 10, i.e., pulses, pulse bursts or trains, low energy or high energy shocks, is applied through output circuitry 37 to the applicable heart lead(s) 40 for delivery to preselected locations within the heart. These and other leads may also convey sensed signals from electrodes in or on the heart or at other appropriate locations of the patient's body, and may acquire the ECG morphologies, for return to the device (e.g., for application to the sense amplifier, or for storage in memory and subsequent retrieval by the programming console via telemetry).

FIG. 2 shows the header 50 of case 11 which incorporates an electrical connector block 52 including receptacles (e.g., 54, 55, 56) for receiving the heart leads 40. The distal ends of the leads are inserted by the physician into the appropriate preselected locations within the patient's heart, and are then connected to the circuitry within the function generator of the device 10 by means of the plug connectors at the proximal ends of the leads, which are inserted into the proper receptacles. It should be emphasized that the connector portion of the header shown in FIG. 2 is not intended to represent a complete connector. As pointed out above, other leads may be plugged into appropriate receptacles for delivering sense signals from the heart or elsewhere in the body, including signals indicative of ECG morphology.

The receptacles 54, 55, 56 of the connector block 52 are sized or otherwise coded to avoid or prevent acceptance of the plug-in connector of any lead other than the proper lead for electrical connection to the internal circuitry of device 10. Once the leads are in place and connected to the device various tests are performed to assure that they are properly seated, such as to detect capture and suitable threshold. Various unique aspects of the connector portion of the device will be discussed in greater detail presently.

Figures 3, 4:
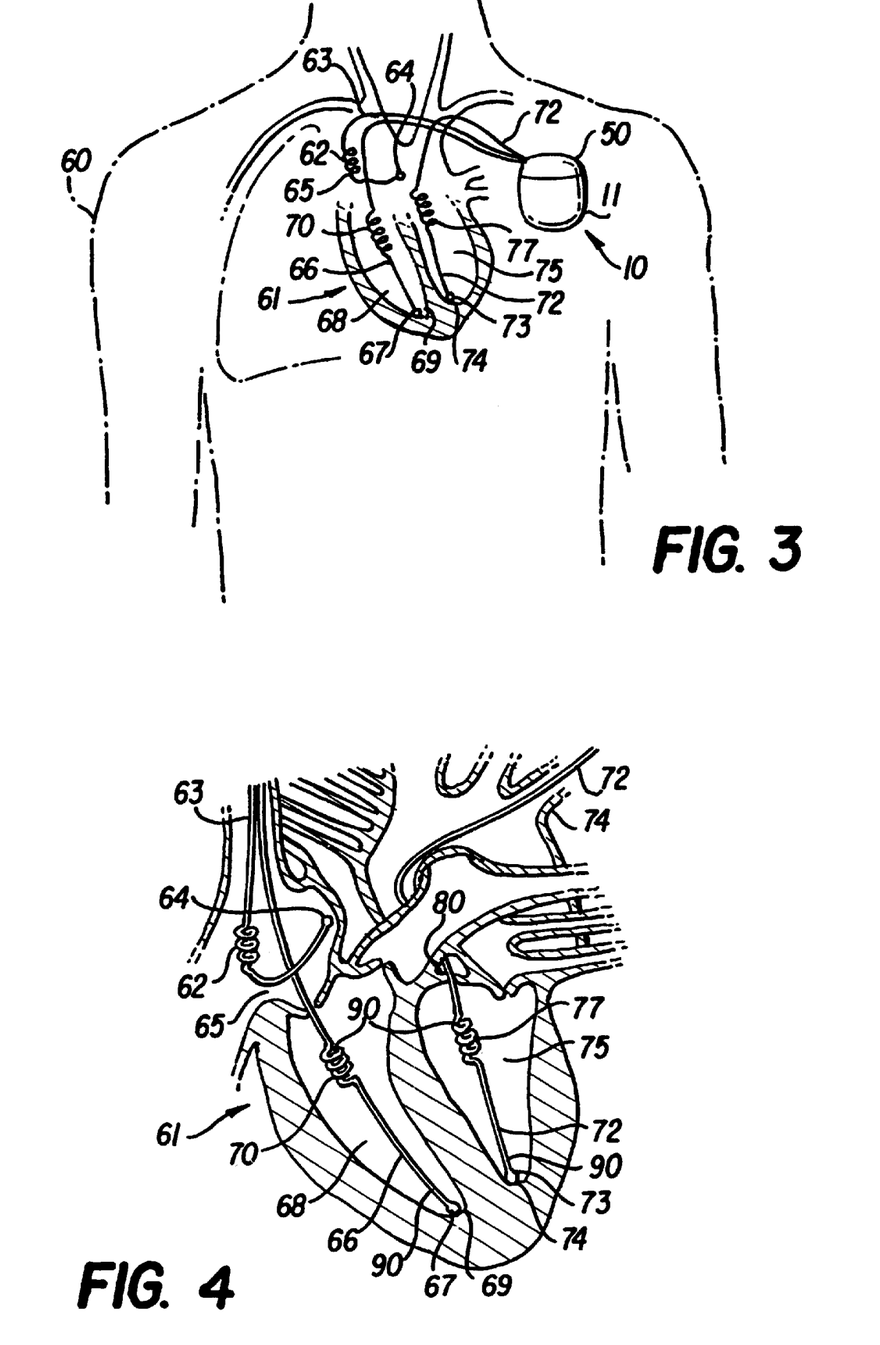
FIG. 3 is a partial front view of a patient, shown in phantom, illustrating some of the internal organs including the heart and related vascular system to show the relative locations of the implanted device and its related electrical leads as inserted into the heart.
FIG. 4 is a simplified anterior view of the human heart showing the placement of the various leads and associated electrodes in the associated vessels and chambers thereof.

FIGS. 3 and 4 represent a phantom partial front view of a patient 60 illustrating the position of the device case 11 implanted in the left pectoral region of the chest, and a more detailed anterior section view of the heart 61 showing the placement of the various heart leads and electrodes. Connected to the function generator 16 of device 10 via connector block 52 is an atrial lead 63 which has its bipolar electrode 64 positioned in close proximity to excitable tissue in the right atrium 65 of the patient's heart 61, for sensing and pacing cardiac activity of the atrium. Right atrial lead 63 has a coil electrode 62 coupled by a separate wire in the sheath of the lead to defibrillator shock generator 35 when the lead is inserted into the proper receptacle of connector block 52.

A ventricular lead 66, with a distal electrode 67 positioned at the apex 69 of the right ventricle 68 when the lead is properly seated, is connected at its proximal end to the proper receptacle of connector block 52 of header 50 of case 11 and is used to sense and pace cardiac activity of the right ventricle. Ventricular lead 66 includes a coil electrode 70, which is on a separate electrical wire, but encompassed in the same sheath as the wire connected to electrode 67, for positioning within the right ventricle when lead 66 is properly seated. Defibrillation shocks are applied to coil electrode 70 in the right ventricle 68 to establish an electric field relative to a counter-electrode outside the heart, which is typically the metal can or case 11 that houses the electronics and batteries of device 10. The location of the case implanted in the left pectoral region of the patient's chest assures that the field will be present over a large part of the mass of the ventricular walls.

According to the present invention, separate pacing leads 72 and 66 are implanted in the left and right ventricles 75, 68, respectively, of the patient's heart to allow the ventricles to be paced simultaneously. For purposes of ventricular defibrillation, each of these ventricular leads also has its own separate defibrillation coil (77, 70, respectively). The right ventricular lead 66 is introduced into the right ventricle in the usual manner by venous access, such as via the vena subclavia either by puncture or by a cutdown of the vena cephalica. As noted above, this lead is placed with its distal electrode 67 resident at the apex 69 of the chamber, for electrical stimulation to pace the ventricle 68 and, in the event of ventricular fibrillation, to deliver a defibrillation shock to the ventricle, by application of appropriate electrical signals to the proximal end of the lead via the connector block in the header of the implanted defibrillator.

The right atrial lead 63 provides pacing stimulation via electrode 64 to the right atrial chamber 65 from device 10, and also enables defibrillating shocks to be delivered to its associated coil electrode 62 in that chamber from the defibrillator section of the device to which the atrial lead is also connected at the header. These leads allow stimulation in VVI, VVI-R (by means of an activity sensor in the defibrillator), DDD, DDD-R, AAI, AAI-R, and other modes. The defibrillating shocks can be applied between the coil of the respective lead and the active can 11.

According to the invention, a left ventricular lead 72 is inserted into the left ventricle 73 by advancement into the arteria subclavia 74 which is either punctured or exposed by surgical preparation for access to the arterial system. Alternatively, the left ventricular lead may be implanted by puncture of the truncus brachiocephalicus and insertion through that puncture. Another technique is to surgically expose either the subclavian artery or the brachiocephalic artery and to apply a circular tightening suture ("tabakbeutelnaht"). This assists in tightening up the site of entry to avoid internal bleeding, which is especially important where subsequent anti-coagulation measures are employed by use of platelet inhibitors as is more fully explained below.

It is essential that the outer surface of this lead 72 be of very low thrombogenicity, such as by use of high performance silicone or polyurethane insulation, and by other techniques which will be described presently. It is also important that the lead body be of very small diameter, e.g., in a range from less than about 7 F, so as not to compromise the mechanical function of the aortic valve 80 during retrograde passage into the left ventricle 75 or during the valve's operation in the cardiac cycle.

Advanced materials and fabrication techniques have enabled reductions in size of heart lead diameters for implantable defibrillators to a range of 5 to 7 French (1.66 mm to 2.33 mm) from previous sizes that ranged from 9 to 11 French (i.e., 3.00 mm to 3.66 mm). More recent developments in coated wire techniques have made it possible to produce lead diameters in an even smaller range, of from 4 to 6 French (1.33 mm to 2.00 mm). These small sizes make it much easier to insert the defibrillator leads through the vascular system to the heart, and to place the leads and associated electrodes or poles in the desired position(s) in the appropriate chamber(s) of the heart.

The left ventricular lead 72 has a pacing (and sensing) electrode 73 located at its distal end, which is seated at the apex 74 of left ventricle 75 when the lead is properly and fully inserted in place. This lead also has a defibrillation coil electrode 77. After insertion through the puncture opening in the left subclavian artery or the brachiocephalic artery, the lead 72 is inserted by retrograde passage through the aortic valve 80 into the left ventricle 75, as shown more clearly in FIG. 4.

The major concern in placement of a left ventricular lead lies in the potential generation of a thrombus on the defibrillator coil. A locally formed thrombus especially in that location might embolize into the brain and cause a cerebral stroke, death or major disability. While previous lead materials of choice have been relatively thrombogenic, with standard isolating materials having exhibited several layers of thrombocytes and other thrombotic depositions, particularly at the defibrillator coil, newer surface materials such as iridium oxide coated wires and titanium nitrate coated materials, have demonstrated extremely low thrombogenicity. Therefore, successful placement and maintenance of the left ventricular lead can be achieved with considerably less concern by use of a lead with low thrombogenicity insulation as mentioned above, and having a surface coating of titanium nitrate or iridium oxide, for example, on the electrical wire.

In addition, as mentioned above, a pacing lead may be inserted into the left atrium, either by needle puncture and access to the left atrium through the adjacent distal coronary sinus, which is preferred, or through the atrial septum wall from the right atrium. The purpose is to enable simultaneous pacing of the right and left atrial chambers, and, following an appropriate delay representing the atrioventricular (A-V) delay interval, simultaneous pacing of the right and left ventricles by application of the pacing stimuli to the respective leads.

The additional use of systemically applied heparin (in the peri-operative setting) and especially the use of orally administered ticlopidine as thrombocyte inhibitors over a limited period of time (e.g., from one to three months following the operation) can serve to prevent the incidence of local thrombus formation until protective connective tissue builds up around the electrode. Animal and human studies have demonstrated that a very thin protective layer of connective tissue can be formed in as little as three to six weeks. Monocytes, which are present in the blood, deposit on the surface and convert into fibroblast, which builds this connective tissue. It is essential that the process should take place for a sufficient period of buildup of the connective tissue to shield the foreign body and later leave it as a neutral foreign body, to prevent thrombus formation. This may be assisted as well by application to the lead surface of inhibitors of plasmatic coagulation, such as heparin and hirudin, and by inhibitors of platelet aggregation, such as aspirin, membrane or surface receptor GP (glycoprotein) IIb/IIIa blockers (i.e., platelet inhibitors that act on the GP IIb/IIIa receptor), or other inhibitors of the fibrinogen binding receptor.

These inhibitors may be applied by incorporating them into a biodegradable carrier which is used to coat the surfaces of interest, as disclosed in co-pending U.S. patent application Ser. No. 08/798,333 of E. Alt et al, now U.S. Pat. No. 5,788,979 the specification of which is incorporated by reference herein. According to that invention, the carrier itself is a substance or composition that undergoes continuous degradation or disintegration within the body to self-cleanse the coated surface as well as to release thrombus inhibitors incorporated in the coating. The carrier degrades slowly through hydrolytic, enzymatic or other degenerative processes. Blood components including albumin, adhesive proteins, and thrombocytes are unable to adhere to the protected surface because of the continuous cleansing action along the entire surface. Additionally, the added inhibitors undergo slow release with the controlled degradation of the carrier.

The coating carrier is a synthetic or naturally occurring biodegradable polymer such as aliphatic and hydroxy polymers of lactic acid, glycolic acid, mixed polymers and blends, polyhydroxybutyrates and polyhydroxy-valeriates and corresponding blends, or polydioxanon, modified starch, gelatine, modified cellulose, caprolactaine polymers, poly-acrylic acid, polymethacrylic acid or derivatives thereof, which will not alter the structure or function of the material to which it is superficially applied. The biodegradable polymer disintegrates with consequent slow release of the drugs (i.e., the inhibitors) incorporated therein, while in contact with blood or other body fluids.

The carrier layer (which is represented by reference number 90 in FIG. 4 for the sake of illustration, but which may be restricted to portions of the respective leads at and near the electrodes) is applied in an extremely thin and tightly adherent layer less than about 100 microns ($\mu$m) thick—even a coating of only 10 $\mu$m—to the surface of the lead. It is prepared as a liquid or semi-liquid phase of the selected carrier material, and applied in a very thin, paint-like layer or multiple layers by dipping or spraying, followed by drying of the carrier. Its disintegration over time may be carefully controlled, and the disintegration makes place without harm to the tissue, blood or other fluids of the body. The selected inhibitors are incorporated in the carrier coating for timed release therefrom as the carrier disintegrates, by virtue of the controlled time of disintegration of the carrier. The time of disintegration may be adjusted by varying the thickness of the carrier coating or of its multiple layer along with and/or as well as by factors such as the biodegradable carrier material(s) selected and the specific time release characteristics of the incorporated drugs. Applying the biodegradable coating in multiple, different layers (i.e., with different inhibitors/additives) of the same or different thickness can provide prolonged action of a particular inhibitor and enable different beneficial actions to occur at predetermined different intervals of time. For example, the innermost coating layer (relative to the lead and/or electrode surface) may be intended to provide the most prolonged action, while the outermost layer is intended primarily for near term response to its initial exposure to blood. After the biodegradable material has completely disintegrated, which may be set as a period of several weeks or months, thrombus formation continues to be inhibited because by the time the controlled period has elapsed the lead will have been coated by connective tissue.

Application of the carrier coating with added anti-inflammatory or anti-coagulant substances therein to the electrode(s) of the lead inhibits a build-up of scar tissue on the electrode at the electrode-myocardial (endocardial) tissue interface in the case of the pacing electrode, or the formation of thrombi in the case of the defibrillation electrode, or at the site of passage through the aortic valve, to prevent adhesion of the lead to the leaflets of the valve. The amount and dosage of the drug(s) incorporated into and released from the biodegradable carrier may be prescribed to suppress the thrombus formation process locally without otherwise affecting normal systemic functions.

With both the left ventricular lead 72 and the right ventricular lead 66 in place, pacing stimulation from the implanted device 10 may be applied simultaneously to both pacing electrodes 73 and 67 of the respective ventricular chambers. By synchronizing the mechanical contraction from the apex of the heart, considerable improvement in hemodynamics can be achieved in many patients. This is partly a result of a more organized contraction, and partly an avoidance of mitral regurgitation, which often additionally compromises the left ventricular function. Hemodynamic improvement has been shown to reduce the occurrence of fibrillation, and thus, the need for defibrillation, with concomitant savings of energy consumption and increased longevity of the implanted device.

Use of pacing electrodes in both the right and left ventricles avoids many problems associated with prior art left ventricle stimulation. And the retrograde ventricular access through the aorta and aortic valve 80 to the left ventricle 75 is achieved by a relatively simple procedure of puncturing the subclavia or the brachiocephalic artery which can be done under local anesthesia, in avoidance of a need for and risks of major surgical measures.

Moreover, placement of a defibrillation coil 77 in the left ventricle as well as a defibrillation coil 70 in the right ventricle allows defibrillation shocks to be delivered solely between these two electrodes, to considerably reduce the energy requirements of a successful shock. Even where individual parameters of thorax geometry and of the heart within the thorax may necessitate use of the two ventricular coils as a single pole and of the defibrillator case as the other pole, a substantial reduction in the energy consumption needed for defibrillation is achieved. By virtue of creating a substantially equal electric field distribution around the two ventricular electrodes and through the ventricular chambers, it is possible to implant a defibrillator having a maximum available energy output of only 15 joules to achieve successful defibrillation with adequate safety margin, even in patients with an enlarged heart. This means that the implanted device of the invention can be produced with a weight considerably less than 50 grams and a volume of less than 30 cc, which compares favorably in weight and size with the DDD pacing-limited device types which were being implanted only a few years ago. Cosmetic advantages and reduction of patient discomfort are added advantages of the size and weight reductions.

Provision of a coil on the right atrial lead 63 enables treatment of atrial fibrillation, with a capability of four-way application of shocks between the defibrillation coil 62 in the right atrium 65 and defibrillation coil 77 in the left ventricle 75, or defibrillation coil 70 in the right ventricle 68, or the case 11,—or of coil 62 against a combination of defibrillation coils 77 and 70 and case 11 together—to create a relatively homogeneous electric field through the atria.

Additionally, the lead 63 in the right atrium facilitates discrimination between supraventricular tachycardia (originating from outside the ventricle, generally either from the SA node or AV node or the atrium) and ventricular tachycardia. It provides a knowledge of the underlying atrial rhythm as well as of the ventricular rhythm by detecting the local ECG simultaneously at the left and right ventricles and the right atrium, for comparison. If a complete dissociation between the ventricular arrhythmia and the atrial rhythm is found, the diagnosis of ventricular tachycardia would be virtually conclusive. In that case, an anti-tachycardia therapy may be delivered by the device and associated lead(s) to the ventricle. However, if the discrimination algorithm determines the atrium to be the primary source of the present tachycardia, the therapeutic intervention would instead be generated and delivered as appropriate to treat a diagnosed primary atrial tachyrhythmia.

Although a presently contemplated best mode of practicing the invention has been described herein, it will be recognized by those skilled in the art to which the invention pertains from a consideration of the foregoing description of a presently preferred embodiment, that variations and modifications of this exemplary embodiment and method may be made without departing from the true spirit and scope of the invention. Accordingly, it is intended that the invention shall be limited only by the appended claims and the rules and principles of applicable law.

What is claimed is:

1. An implantable medical interventional device adapted to provide therapy to a patient to treat cardiac dysrhythmias, said device comprising a pulse generator and a shock generator for providing a plurality of functions corresponding to different levels of therapy including pulse, low energy and high energy shock waveforms configured to terminate respective dysrhythmias; said pulse generator adapted for pacing the patient's heart by generating stimulating electrical pulses therefor; and a pair of thin leads dimensioned for insertion respectively into the left and right ventricles of the patient's heart when said device is implanted, said pair of thin leads being coupled to said pulse generator and said pulse generator being adapted to energize said pair of thin leads in unison for simultaneous application of said stimulating electrical pulses to the left and right ventricles when said pair of thin leads are inserted respectively therein, each of said leads including a respective electrode adapted to be positioned in stimulating relation to cardiac tissue in a respective one of said ventricles when said leads are inserted therein and, when said leads are energized in unison by said pulse generator, to simultaneously pace said left and right ventricles; the lead dimensioned for insertion into the left ventricle having an insulative sheath composed of a material of low thrombogenicity and coated at least in part with a biodegradable material to inhibit thrombus formation on the respective lead.

2. The device of claim 1, wherein said material of low thrombogenicity is selected from the group consisting of silicone and polyurethane.

3. The device of claim 1, wherein said biodegradable material coating includes at least one platelet inhibitor incorporated therein for timed release during disintegration of said coating.

4. The device of claim 3, wherein said at least one platelet inhibitor is iloprost.

5. The device of claim 3, wherein said biodegradable material coating further includes a plasmatic coagulation inhibitor incorporated therein for timed release during disintegration of said coating.

6. The device of claim 5, wherein said plasmatic coagulation inhibitor is selected from the group consisting of heparin and hirudin.

7. An implantable medical interventional device adapted to provide therapy to a patient to treat cardiac dysrhythmias, said device comprising a pulse generator and a shock generator for providing a plurality of functions corresponding to different levels of therapy including pulse, low energy and high energy shock waveforms configured to terminate respective dysrhythmias; said pulse generator adapted for pacing the patient's heart by generating stimulating electrical pulses therefor; and a pair of thin leads dimensioned for insertion respectively into the left and right ventricles of the patient's heart when said device is implanted, said pair of thin leads being coupled to said pulse generator and said pulse generator being adapted to energize said pair of thin leads in unison for simultaneous application of said stimulating electrical pulses to the left and right ventricles when said pair of thin leads are inserted respectively therein, each of said leads including a respective electrode adapted to be positioned in stimulating relation to cardiac tissue in a respective one of said ventricles when said leads are inserted therein and, when said leads are energized in unison by said pulse generator, to simultaneously pace said left and right ventricles; said shock generator being adapted for defibrillating the patient's heart by generating higher voltage electrical shock waveforms therefor; and each of said pair of leads further including a defibrillation coil coupled to said shock generator and adapted to be positioned within a respective one of said ventricles and, when energized by said shock generator, for applying an electrical shock waveform to establish a substantially homogeneous electric field of sufficient electrical energy in the ventricles for defibrillation thereof.

8. The device of claim 7, wherein the defibrillation coils on respective ones of said pair of leads constitute defibrillation poles adapted to be energized simultaneously with their respective leads so that the defibrillation coil on the lead adapted to be positioned in the left ventricle is the anode and the defibrillation coil on the lead adapted to be positioned in the right ventricle is the cathode.

9. The device of claim 7, including a metal case housing said function generator, and wherein the defibrillation coils on said pair of leads constitute a defibrillation pole adapted to be energized simultaneously with their respective leads to act as an anode, in conjunction with said case constituting a defibrillation pole adapted when energized together with said defibrillation coils to act as a cathode.

10. The device of claim 7, further including an atrial pacing lead coupled to said pulse generator, said atrial pacing lead including a right atrial defibrillation coil, said right atrial defibrillation coil being coupled to said shock generator for defibrillation of the atrial chambers.

11. An implantable defibrillator, comprising a shock generator for generating electrical shock waveforms, a right ventricular lead including a defibrillation electrode coupled to said shock generator and adapted to be positioned in the right ventricle of a patient's heart for delivery of electrical shock waveforms thereto, a left ventricular lead including a defibrillation electrode coupled to said shock generator and adapted to be positioned in the left ventricle of the patient's heart for delivery of electrical shock waveforms thereto, and means for selectively applying said electrical shock waveforms of predetermined energy content simultaneously to said right and left ventricular defibrillation electrodes to establish a substantially homogeneous electric field distribution in the ventricles for defibrillation thereof.

12. The defibrillator of claim 11, including a metal case for said shock generator, and wherein said selectively applying means is adapted to apply said electrical shock waveforms either between said right and left ventricular defibrillation electrodes as separate poles, or between said right and left ventricular defibrillation electrodes as one pole and said metal case as another pole, for defibrillation of the ventricles.

13. The defibrillator of claim 11, further comprising a metal case for said shock generator, a right atrial lead including a defibrillation electrode coupled to said shock generator and adapted to be positioned in the right atrium of the patient's heart for delivery of electrical shock waveforms thereto, and wherein said selectively applying means is adapted to apply said electrical shock waveforms between said right atrial defibrillation electrode and one of said right ventricular defibrillation electrode, said left ventricular defibrillation electrode, and said metal case, for defibrillation of the atria.

14. The defibrillator of claim 11, further comprising a pacing pulse generator of stimulating pacing pulses, separate pacing electrodes on each of said right and left ventricular leads respectively coupled to said pulse generator and adapted to be positioned respectively in the right and left ventricles of the patient's heart for selective delivery of stimulating pacing pulses simultaneously thereto, and an atrial pacing lead including an electrode coupled to said pulse generator and adapted to be positioned in the right atrium of the patient's heart for selective delivery of stimulating pacing pulses thereto.

15. A device-implemented method of treating cardiac dysrhythmias with an implantable medical interventional device adapted to deliver therapy to an implant patient, wherein the device possesses the capability to provide at least pacing therapy to the patient's heart, said method including the steps of:

sensing a need for ventricular pacing; and responding to said sensed need by delivering pacing pulses simultaneously to both ventricles of the patient's heart; and wherein said device possesses the capability to provide a plurality of functions corresponding to different therapies for treatment of dysrhythmias, and further including the steps of:

sensing ventricular fibrillation; and responding to said sensed ventricular fibrillation by delivering an electrical shock waveform simultaneously to both ventricles of the patient's heart to establish an electric field of relatively uniform distribution and sufficient electrical energy simultaneously in the ventricles for defibrillation thereof.

16. The device-implemented method of claim 15, including delivering sense signals indicative of ventricular fibrillation to said device from separate right and left ventricular leads coupled thereto, and delivering electrical shock waveforms simultaneously to said right and left ventricular leads from a shock generator of said device.

17. The device-implemented method of claim 15, further including the steps of:

sensing atrial fibrillation; and responding to said sensed atrial fibrillation by delivering an electrical shock waveform between the right atrium and selectively either of the right and left ventricles of the patient's heart to establish an electric field of sufficient electrical energy through the atrium for defibrillation thereof.

18. The device-implemented method of claim 15, including delivering sense signals indicative of ventricular fibrillation to said device from separate right and left ventricular leads coupled thereto, delivering sense signals indicative of atrial fibrillation to said device from a right atrial lead coupled thereto, and delivering electrical shock waveforms from a shock generator of said device to said right atrial lead and said right and left ventricular leads as necessary for defibrillation.

19. An implantable medical interventional device adapted to provide therapy to a patient to treat cardiac dysrhythmias, said device comprising therapy-providing apparatus responsive to different types of dysrhythmia for providing a level of therapy appropriate respectively thereto, including electrical pulse and shock waveforms of sufficiently high energy content to pace and defibrillate respectively; and therapy-application apparatus for application of therapy simultaneously to both ventricles of the patient's heart, including a right ventricular lead and a left ventricular lead each including a pacing electrode and a defibrillating electrode separately coupled to said therapy-providing apparatus.

20. A method for providing a patient with an implanted medical interventional device to treat cardiac dysrhythmias, wherein the device performs a plurality of functions corresponding to different levels of therapy for treatment of different types of dysrhythmias, and responds to each different type of dysrhythmia to generate any of a plurality of electrical waveform therapies, including at least electrical pulse and shock waveform therapies, appropriate to terminate the respective sensed dysrhythmia, the method comprising the steps of implanting said device in the patient, implanting an electrical lead in the patient that includes an electrode for delivering at least one of said pulse and shock waveform therapies from the device in each of the right and left ventricles of the patient's heart, and electrically connecting each lead to said device to enable said electrode thereof to receive at least one of the therapies; and prior to implanting the lead, the step of coating at least a portion of the electrical lead to be implanted in the left ventricle with a biodegradable carrier impregnated with a thrombus inhibitor adapted to be time-released into blood in the locality of said portion of the lead in the left ventricle during disintegration of said carrier, to avoid embolization of a thrombus thereat.

21. The method of claim 20, including the step of selecting the biodegradable carrier to degrade harmlessly in the blood with negligible systemic impact, and selecting the thrombus inhibitor from the group consisting of ticlopidine, aspirin, heparin, and hirudin.

22. The method of claim 21, including the step of selecting at least one physical parameter of the biodegradable carrier to fix complete disintegration thereof within a period of from about one month to about three months from the time of implanting the lead, for time-release of the thrombus inhibitor over said period.

23. A method for providing a patient with an implanted medical interventional device to treat cardiac dysrhythmias, wherein the device performs a plurality of functions corresponding to different levels of therapy for treatment of different types of dysrhythmias, and responds to each different type of dysrhythmia to generate any of a plurality of electrical waveform therapies, including at least electrical pulse and shock waveform therapies, appropriate to terminate the respective sensed dysrhythmia, the method comprising the steps of implanting said device in the patient, implanting an electrical lead that includes an electrode for delivering at least one of said pulse and shock waveform therapies from the device in each of the right and left ventricles of the patient's heart, and electrically connecting each lead to said device to enable said electrode thereof to receive at least one of the therapies; and, wherein the step of implanting the electrical lead in the left ventricle includes puncturing one of the subclavian and brachiocephalic arteries, inserting the lead through the puncture, and advancing the lead through the aortic valve into the left ventricle until said electrode is properly located therein.

24. The method of claim 23, wherein each said ventricular lead includes both a pacing electrode at the distal end of the lead and a defibrillating electrode proximal of the pacing electrode, and the step of advancing the lead through the aortic valve into the left ventricle includes placing the pacing electrode in proximity to excitable cardiac tissue of the left ventricle.

25. The method of claim 24, including the step of applying pulse therapy to the pacing electrodes of both the right and left ventricular leads for pacing the ventricles simultaneously, whereby to reduce the duration of the QRS complex of the patient's electrocardiogram.

26. The method of claim 24, including the steps of sensing ventricular fibrillation and thereupon applying shock waveform therapy to the defibrillating electrodes of both the right and left ventricular leads simultaneously, whereby to improve uniformity of the electric field distribution through the ventricles to terminate the ventricular fibrillation.

27. The method of claim 26, wherein the step of applying said shock waveform therapy to the defibrillating electrodes of both the right and left ventricular leads simultaneously includes applying said shock waveform therapy to the defibrillating electrode in the left ventricle as the anode and to the defibrillating electrode in the right ventricle as the cathode.

28. The method of claim 26, wherein said device is implanted in a pectoral region of the patient, and the step of applying said shock waveform therapy to the defibrillating electrodes of both the right and left ventricular leads simultaneously includes applying said shock waveform therapy to said defibrillating electrodes in the ventricles as the anode and to an electrically conductive case in which the therapy generator of said device is housed as the cathode.

29. The method of claim 24, including the steps of implanting an electrical lead with a pacing electrode and a defibrillating electrode thereon in the right atrium of the patient's heart, and applying said shock waveform therapy to the defibrillating electrodes of both the right atrial lead and the left ventricular lead simultaneously to terminate atrial fibrillation.

30. The method of claim 29, including the step of selecting leads to be implanted in the right atrium, right ventricle, and left ventricle of the patient's heart which are covered with an insulating sheath selected from a group comprising silicone and polyurethane, and in which the sheath is coated with a material selected from the group consisting of iridium oxide and titanium nitrate.

31. The method of claim 24, including the steps of detecting the local ECG at the left and right ventricles, and comparing the characteristics of size and morphology thereof for diagnosis of cardiac activity from which to discriminate ventricular and supraventricular tachycardias from one another.

32. The method of claim 23, including the steps of administering a platelet inhibitor into the patient's vascular system for a limited period of time to facilitate healing and a build-up of connective tissue on electrodes of the lead implanted in the left ventricle to avoid interference with operation of the aortic valve.

33. A method for providing therapy to a patient from a medical interventional device adapted to be implanted to treat cardiac dysrhythmias, comprising the steps of simultaneously stimulating the right and left ventricles of the patient's heart to perform ventricular pacing for enhancing hemodynamics, and defibrillating the heart by applying electrical defibrillation shocks to a point in the left ventricle to terminate ventricular fibrillation.

* * * * *